United States Patent
Appel et al.

(10) Patent No.: US 6,432,900 B1
(45) Date of Patent: Aug. 13, 2002

(54) LIGAND AND COMPLEX FOR CATALYTICALLY BLEACHING A SUBSTRATE

(75) Inventors: Adrianus Cornelis Appel; Ronald Hage, both of Vlaardingen (NL); David Tetard, Wirral (GB); Robin Stefan Twisker, Vlaardingen (NL)

(73) Assignee: Unilever Home & Personal Care USA, Division of Conopco, Inc., Greenwich, CT (US)

( * ) Notice: Subject to any disclaimer, the term of this patent is extended or adjusted under 35 U.S.C. 154(b) by 26 days.

(21) Appl. No.: 09/650,148

(22) Filed: Aug. 29, 2000

(30) Foreign Application Priority Data

Sep. 1, 1999 (WO) .............. PCT/GB99/02876
Feb. 29, 2000 (GB) .............. 0004854

(51) Int. Cl.$^7$ ................. C11D 7/26
(52) U.S. Cl. ........ 510/376; 510/312; 510/313; 510/314; 510/499; 510/500; 252/186.33; 544/180; 544/215
(58) Field of Search ............... 510/312, 313, 510/314, 376, 499, 500; 252/186.33; 544/180, 215

(56) References Cited

FOREIGN PATENT DOCUMENTS

| | | |
|---|---|---|
| DE | 19714122 | 4/1997 |
| DE | 19721886 | 5/1997 |
| EP | 0 040 131 | 4/1985 |
| EP | 0 382 583 | 8/1990 |
| EP | 0 924 281 | 12/1997 |
| EP | 0 909 809 | 9/1998 |
| JP | 6-256512 | 9/1994 |
| JP | 10-279411 | 10/1998 |
| JP | 2000/03497 | 2/2000 |
| WO | 90/12050 | 10/1990 |
| WO | 94/04485 | 3/1994 |
| WO | 95/19347 | 7/1995 |
| WO | 95/27772 | 10/1995 |
| WO | 95/34628 | 12/1995 |
| WO | 96/06154 | 2/1996 |
| WO | 97/07124 | 2/1997 |
| WO | 97/38074 | 10/1997 |
| WO | 97/48710 | 12/1997 |
| WO | 97/48787 | 12/1997 |
| WO | 00/12667 | 3/2000 |
| WO | 00/12808 | 3/2000 |

OTHER PUBLICATIONS

Journal of Surfactants and Detergents, vol. 1, No. 2 (Apr. 1998), "Oxygen Bleaching Systems in Domestic Laundry" by Neil J. milne, pp. 253–261.
International Search Report.
J. Chem. Soc. No. 16, 1999, pp. 2751–258.
J. Chem. Soc. No. 7, 1998, pp. 1085–1086.
J. Chem. Soc. No. 11, 1989, pp. 2079–2082.
J. Chem. Soc. No. 3, 1992, pp. 361–365.
Abstract 119:236429 Mar. 1993.
Abstract 129:269414 Feb. 1998.

*Primary Examiner*—Gregory Delcotto
(74) *Attorney, Agent, or Firm*—Milton L. Honig

(57) ABSTRACT

The invention relates to ligands or complexes useful as catalysts for catalytically bleaching substrates with atmospheric oxygen, and as catalysts in the of treatment of textiles such as laundry fabrics whereby bleaching by atmospheric oxygen is catalysed after the treatment. The ligand is of the general formula:

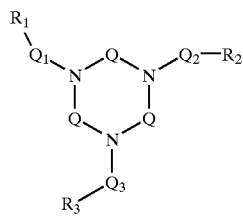

wherein $R_1$, $R_2$, and $R_3$ independently represent a group selected from hydrogen, hydroxyl, halogen, —NH—C(NH)NH$_2$, —R and —OR, wherein R=alkyl, alkenyl, cycloalkyl, heterocycloalkyl, aryl, heteroaryl or a carbonyl derivative group, R being optionally substituted by one or more functional groups, and provided that two of $R_1$, $R_2$ and $R_3$ are coordinating groups and one of $R_1$, $R_2$ and $R_3$ is a non-coordinating group;

Q independently represents a group selected from $C_{2-3}$-alkylene optionally substituted by H, benzyl or $C_{1-8}$-alkyl; and $Q_1$, $Q_2$ and $Q_3$ independently represent specified linking groups.

6 Claims, No Drawings

LIGAND AND COMPLEX FOR CATALYTICALLY BLEACHING A SUBSTRATE

FIELD OF INVENTION

This invention relates to a class of ligand or complex useful as catalysts for catalytically bleaching substrates with atmospheric oxygen, and as catalysts in the treatment of textiles such as laundry fabrics whereby bleaching by atmospheric oxygen is catalysed after the treatment.

BACKGROUND OF INVENTION

Peroxygen bleaches are well known for their ability to remove stains from substrates. Traditionally, the substrate is subjected to hydrogen peroxide, or to substances which can generate hydroperoxyl radicals, such as inorganic or organic peroxides. Generally, these systems must be activated. One method of activation is to employ wash temperatures of 60° C. or higher. However, these high temperatures often lead to inefficient cleaning, and can also cause premature damage to the substrate.

A preferred approach to generating hydroperoxyl bleach radicals is the use of inorganic peroxides coupled with organic precursor compounds. These systems are employed for many commercial laundry powders. For example, various European systems are based on tetraacetyl ethylenediamine (TAED) as the organic precursor coupled with sodium perborate or sodium percarbonate, whereas in the United States laundry bleach products are typically based on sodium nonanoyloxybenzenesulfonate (SNOBS) as the organic precursor coupled with sodium perborate.

Precursor systems are generally effective but still exhibit several disadvantages. For example, organic precursors are moderately sophisticated molecules requiring multi-step manufacturing processes resulting in high capital costs. Also, precursor systems have large formulation space requirements so that a significant proportion of a laundry powder must be devoted to the bleach components, leaving less room for other active ingredients and complicating the development of concentrated powders. Moreover, precursor systems do not bleach very efficiently in countries where consumers have wash habits entailing low dosage, short wash times, cold temperatures and low wash liquor to substrate ratios.

Alternatively, or additionally, hydrogen peroxide and peroxy systems can be activated by bleach catalysts, such as by complexes of iron and the ligand N4Py (i.e. N, N-bis(pyridin-2-yl-methyl)-bis(pyridin-2-yl)methylamine) disclosed in WO95/34628, or the ligand Tpen (i.e. N, N, N', N'-tetra(pyridin-2-yl-methyl)ethylenediamine) disclosed in WO97/48787. According to these publications, molecular oxygen may be used as the oxidant as an alternative to peroxide generating systems. However, no role in catalysing bleaching by atmospheric oxygen in an aqueous medium is reported.

It has long been thought desirable to be able to use atmospheric oxygen (air) as the source for a bleaching species, as this would avoid the need for costly hydroperoxyl generating systems. Unfortunately, air as such is kinetically inert towards bleaching substrates and exhibits no bleaching ability. Recently some progress has been made in this area. For example, WO 97/38074 reports the use of air for oxidising stains on fabrics by bubbling air through an aqueous solution containing an aldehyde and a radical initiator. A broad range of aliphatic, aromatic and heterocyclic aldehydes is reported to be useful, particularly para-substituted aldehydes such as 4-methyl-, 4-ethyl- and 4-isopropyl benzaldehyde, whereas the range of initiators disclosed includes N-hydroxysuccinimide, various peroxides and transition metal coordination complexes.

However, although this system employs molecular oxygen from the air, the aldehyde component and radical initiators such as peroxides are consumed during the bleaching process. These components must therefore be included in the composition in relatively high amounts so as not to become depleted before completion of the bleaching process in the wash cycle. Moreover, the spent components represent a waste of resources as they can no longer participate in the bleaching process.

Accordingly, it would be desirable to be able to provide a bleaching system based on atmospheric oxygen or air that does not rely primarily on hydrogen peroxide or a hydroperoxyl generating system, and that does not require the presence of organic components such as aldehydes that are consumed in the process. Moreover, it would be desirable to provide such a bleaching system that is effective in aqueous medium.

It may also be noted that the known art teaches a bleaching effect only as long as the substrate is being subjected to the bleaching treatment. Thus, there is no expectation that hydrogen peroxide or peroxy bleach systems could continue to provide a bleaching effect on a treated substrate, such as a laundry fabric after washing and drying, since the bleaching species themselves or any activators necessary for the bleaching systems would be assumed to be removed from the substrate, or consumed or deactivated, on completing the wash cycle and drying.

It would be therefore also be desirable to be able to treat a textile such that, after the treatment is completed, a bleaching effect is observed on the textile. Furthermore, it would be desirable to be able to provide a bleach treatment for textiles such as laundry fabrics whereby residual bleaching occurs when the treated fabric has been treated and is dry.

SUMMARY OF INVENTION

We have found a novel class of ligand or complex that is surprisingly effective in catalysing the bleaching of substrates using atmospheric oxygen or air.

Accordingly, in a first aspect, the present invention provides of the general formula:

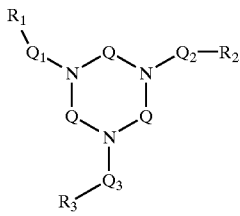

wherein $R_1$, $R_2$, and $R_3$ independently represent a group selected from hydrogen, hydroxyl, halogen, —NH—C(NH)NH$_2$, —R and —OR, wherein R=alkyl, alkenyl, cycloalkyl, heterocycloalkyl, aryl, heteroaryl or a carbonyl derivative group, R being optionally substituted by one or more functional groups E, further specified below;

Q independently represents a group selected from $C_{2-3}$-alkylene optionally substituted by H, benzyl or $C_{1-8}$-alkyl; and $Q_1$, $Q_2$ and $Q_3$ independently represent linking groups, further specified below, provided that two of $R_1$, $R_2$ and $R_3$ are coordinating groups and one of $R_1$, $R_2$ and $R_3$ is a non-coordinating group, and with the proviso that the following ligands are excluded:
1,4-bis(N-methyl-imidazol-2ylmethyl)-1,4,7-triazacyclononane;
1,4-bis(N-methyl-imidazol-2ylmethyl)-7-acetate-1,4,7-triazacyclononane;
1,4-bis(pyridin-2-ylmethyl)-7-ethyl-1,4,7-triazacyclononane;
1,4-bis(quinolin-2-ylmethyl)-7-ethyl-1,4,7-triazacyclononane;
1,4-bis(pyrazol-1-ylmethyl)-7-ethyl-1,4,7-triazacyclononane;
1,4-bis(3,5-dimethylpyrazol-1-ylmethyl)-7-ethyl-1,4,7-triazacyclononane;
1,4-bis(N-methylimidazol-2-ylmethyl)-7-ethyl-1,4,7-triazacyclononane;
1,4-bis(N-isopropylacetamido)-7-ethyl-1,4,7-triazacyclononane; and
1,4-bis(N-methylacetamido)-7-ethyl-1,4,7-triazacyclononane.

In a second aspect, the present invention provides a complex of the ligand and a transition metal.

An advantage of the class of ligand and complex according to the present invention is that the complex can catalyse bleaching of a substrate by atmospheric oxygen, thus permitting its use in a medium such as an aqueous medium that is substantially devoid of peroxygen bleach or a peroxy-based or -generating bleach system. We have also found that complexes of this class are surprisingly effective in catalysing bleaching of the substrate by atmospheric oxygen after treatment of the substrate.

Advantageously, the ligand or complex according to the present invention permits all or the majority of the bleaching species in the medium (on an equivalent weight basis) to be derived from atmospheric oxygen. Thus, the medium can be made wholly or substantially devoid of peroxygen bleach or a peroxy-based or -generating bleach system. Furthermore, the complex is a catalyst for the bleaching process and, as such, is not consumed but can continue to participate in the bleaching process. Thus, the ligand or complex can provide a catalytically activated bleaching system which is based on atmospheric oxygen, is therefore both cost-effective and environmentally friendly. Moreover, a bleaching system can be provided that is operable under unfavourable wash conditions which include low temperatures, short contact times and low dosage requirements. Furthermore, the catalyst is effective in an aqueous medium and is therefore particularly applicable to bleaching of laundry fabrics. Therefore, whilst the catalyst according to the present invention may be used for bleaching any suitable substrate, the preferred substrate is a laundry fabric. Bleaching may be carried out by simply leaving the substrate in contact with the medium for a sufficient period of time. Preferably, however, the aqueous medium on or containing the substrate is agitated.

A further advantage is that, by enabling a bleaching effect even after the textile has been treated, the benefits of bleaching can be prolonged on the textile. Furthermore, since a bleaching effect is conferred to the textile after the treatment, the treatment itself, such as a laundry wash cycle, may for example be shortened. Moreover, since a bleaching effect is achieved by atmospheric oxygen after treatment of the textile, hydrogen peroxide or peroxy-based bleach systems can be omitted from the treatment substance.

The present invention also extends to a commercial package comprising a bleaching composition comprising a ligand or complex as defined below together with instructions for its use.

The present invention also extends to use of a ligand or complex as defined below in the manufacture of a bleaching composition, the bleaching composition substantially devoid of peroxygen bleach or a peroxy-based or peroxy-generating bleach system.

DETAILED DESCRIPTION OF THE INVENTION

The catalyst may be used as a preformed complex of the ligand and a transition metal. Alternatively, the catalyst may be formed from the free ligand that complexes with a transition metal already present in the water or that complexes with a transition metal present in the substrate. The composition may also be formulated as a composition of the free ligand or a transition metal-substitutable metal-ligand complex, and a source of transition metal, whereby the complex is formed in situ in the medium.

The ligand forms a complex with one or more transition metals, in the latter case for example as a dinuclear complex. Suitable transition metals include for example: manganese in oxidation states II–V, iron II–V, copper I–III, cobalt I–III, titanium II–IV, tungsten IV–VI, vanadium II–V and molybdenum II–VI.

The ligand forms a complex of the general formula (A1):

$$[M_a L_k X_n] Y_m \qquad (A1)$$

in which:

M represents a metal selected from Mn(II)-(III)–(IV)-(V), Cu(I)-(II)-(III), Fe(II)-(III)-(IV)-(V), Co(I)-(II)-(III), Ti(II)-(III)-(IV), V(II)-(III)-(IV)-(V), Mo(II)-(III)-(IV)-(V)-(VI) and W(IV)-(V)-(VI), preferably selected from Fe(II)-(III)-(IV)-(V);

L represents a ligand as herein defined, or its protonated or deprotonated analogue;

X represents a coordinating species selected from any mono, bi or tri charged anions and any neutral molecules able to coordinate the metal in a mono, bi or tridentate manner, preferably selected from $O^{2-}$, $RBO_2^{2-}$, $RCOO^-$, $RCONR^-$, $OH^-$, $NO_3^-$, $NO$, $S^{2-}$, $RS^-$, $PO_4^{3-}$, $PO_3OR^{3-}$, $H_2O$, $CO_3^{2-}$, $HCO_3^-$, $ROH$, $N(R)_3$, $ROO^-$, $O_2^{2-}$, $O_2^-$, $RCN$, $Cl^-$, $Br^-$, $OCN^-$, $SCN^-$, $CN^-$, $N_3^-$, $F^-$, $I^-$, $RO^-$, $ClO_4^-$, and $CF_3SO_3^-$, and more preferably selected from $O^{2-}$, $RBO_2^{2-}$, $RCOO^-$, $OH^-$, $NO_3^-$, $S^{2-}$, $RS^-$, $PO_3^{4-}$, $H_2O$, $CO_3^{2-}$, $HCO_3^-$, $ROH$, $N(R)_3$, $Cl^-$, $Br^-$, $OCN^-$, $SCN^-$, $RCN$, $N_3^-$, $F^-$, $I^-$, $RO^-$, $ClO_4^-$, and $CF_3SO_3^-$;

Y represents any non-coordinated counter ion, preferably selected from $ClO_4^-$, $BR_4^-$, $[MX_4]^-$, $[MX_4]^{2-}$, $PF_6^-$, $RCOO^-$, $NO_3^-$, $RO^-$, $N^+(R)_4$, $ROO^-$, $O_2^{2-}$, $O_2^-$, $Cl^-$, $Br^-$, $F^-$, $I^-$, $CF_3SO_3^-$, $S_2O_6^{2-}$, $OCN^-$, $SCN^-$, $H_2O$, $RBO_2^{2-}$, $BF_4^-$ and $BPh_4^-$, and more preferably selected from $ClO_4^-$, $BR_4^-$, $[FeCl_4]$, $PF_6^-$, $RCOO^-$, $NO_3^-$, $RO^-$, $N^+(R)_4$, $Cl^-$, $Br^-$, $F^-$, $I^-$, $CF_3SO_3^-$, $S_2O_6^{2-}$ $OCN^-$, $SCN^-$, $H_2O$ and $BF_4^-$;

a represents an integer from 1 to 10, preferably from 1 to 4;

k represents an integer from 1 to 10;

n represents an integer from 1 to 10, preferably from 1 to 4;

m represents zero or an integer from 1 to 20, preferably from 1 to 8; and each R independently represents a group selected from hydrogen, hydroxyl, —R' and —OR', wherein R'=alkyl, alkenyl, cycloalkyl, heterocycloalkyl, aryl, heteroaryl or a carbonyl derivative group, R' being optionally substituted by one or more functional groups E, wherein E independently represents a functional group selected from —F, —Cl, —Br, —I, —OH, —OR', —NH$_2$, —NHR', —N(R')$_2$, —N(R')$_3^+$, —C(O)R', —OC(O)R', —COOH, —COO$^-$ (Na$^+$, K$^+$), —COOR', —C(O)NH$_2$, —C(O)NHR', -C(O)N(R')$_2$, heteroaryl, —R', —SR', —SH, —P(R')$_2$, —P(O)(R')$_2$, —P(O)(OH)$_2$, —P(O)(OR')$_2$, —NO$_2$, —SO$_3$H, —SO$_3^-$ (Na$^+$, K$^+$), —S(O)$_2$R', —NHC(O)R', and —N(R')C(O)R', wherein R' represents cycloalkyl, aryl, arylalkyl, or alkyl optionally substituted by —F, —Cl, —Br, —I, —NH$_3^+$, —SO$_3$H, —SO$_3^-$(Na$^+$, K$^+$), —COOH, —COO$^-$(Na$^+$, K$^+$), —P(O)(OH)$_2$, or —P(O)(O$^-$(Na$^+$, K$^+$))$_2$, and preferably each R independently represents hydrogen, optionally substituted alkyl or optionally substituted aryl, more preferably hydrogen or optionally substituted phenyl, naphthyl or C$_{1-4}$-alkyl.

The ligand L is of the general formula (I):

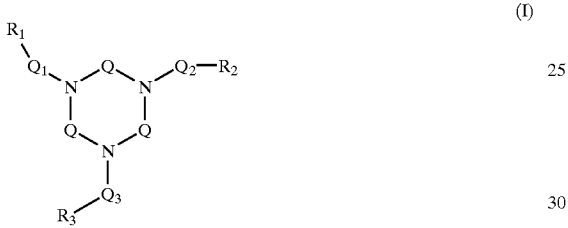
(I)

wherein

R$_1$, R$_2$, and R$_3$ independently represent a group selected from hydrogen, hydroxyl, halogen, —NH—C(NH)NH$_2$, —R and —OR, wherein R=alkyl, alkenyl, cycloalkyl, heterocycloalkyl, aryl, heteroaryl or a carbonyl derivative group, R being optionally substituted by one or more functional groups E;

Q independently represent a group selected from C$_{2-3}$-alkylene optionally substituted by H, benzyl or C$_{1-8}$-alkyl;

Q$_1$, Q$_2$ and Q$_3$ independently represent a group of the formula:

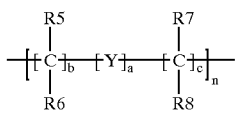

wherein $5 \geq a+b+c \geq 1$; a=0–5; b=0–5; c=0–5; n=1 or 2;

Y independently represents a group selected from —O—, —S—, —SO—, —SO$_2$—, —C(O)—, arylene, alkylene, heteroarylene, heterocycloalkylene, —(G)P—, —P(O)— and —(G)N—, wherein G is selected from hydrogen, alkyl, aryl, arylalkyl, cycloalkyl, each except hydrogen being optionally substituted by one or more functional groups E; and R5, R6, R7, R8 independently represent a group selected from hydrogen, hydroxyl, halogen, —R and —OR, wherein R represents alkyl, alkenyl, cycloalkyl, heterocycloalkyl, aryl, heteroaryl or a carbonyl derivative group, R being optionally substituted by one or more functional groups E, or R5 together with R6, or R7 together with R8, or both, represent oxygen, or R5 together with R7 and/or independently R6 together with R8, or R5 together with R8 and/or independently R6 together with R7, represent C$_{1-6}$-alkylene optionally substituted by C$_{1-4}$-alkyl, —F, —Cl, —Br or —I, provided that two of R1, R2 and R3 are coordinating groups and one of R$_1$, R$_2$ and R$_3$ is a non-coordinating group, and with the proviso that the following ligands are excluded:
1,4-bis(N-methyl-imidazol-2ylmethyl)-1,4,7-triazacyclononane;
1,4-bis(N-methyl-imidazol-2ylmethyl)-7-acetate-1,4,7-triazacyclononane;
1,4-bis(pyridin-2-ylmethyl)-7-ethyl-1,4,7-triazacyclononane;
1,4-bis(quinolin-2-ylmethyl)-7-ethyl-1,4,7-triazacyclononane;
1,4-bis(pyrazol-1-ylmethyl)-7-ethyl-1,4,7-triazacyclononane;
1,4-bis(3,5-dimethylpyrazol-1-ylmethyl)-7-ethyl-1,4,7-triazacyclononane;
1,4-bis(N-methylimidazol-2-ylmethyl)-7-ethyl-1,4,7-triazacyclononane;
1,4-bis(2'-(aceto-N-isopropylamido))-7-ethyl-1,4,7-triazacyclononane; and
1,4-bis(2'-(aceto-N-methylamido))-7-ethyl-1,4,7-triazacyclononane.

Two of R$_1$, R$_2$ and R$_3$ independently represent a group preferably selected from carboxylate, amido, —NH—C(NH)NH$_2$, hydroxyphenyl, an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole. Preferably, two of R$_1$, R$_2$, R$_3$ each independently represent a coordinating group selected from optionally substituted pyridin-2-yl, optionally substituted imidazol-2-yl, optionally substituted imidazol-4-yl, optionally substituted pyrazol-1-yl, and optionally substituted quinolin-2-yl.

Preferably, substituents for groups R$_1$, R$_2$, R$_3$, when representing a heterocyclic or heteroaromatic ring, are selected from C$_{1-4}$-alkyl, aryl, arylalkyl, heteroaryl, methoxy, hydroxy, nitro, amino, carboxyl, halo, and carbonyl.

The groups R5, R6, R7, R8 preferably independently represent a group selected from —H, hydroxy-C$_0$–C$_{20}$-alkyl, halo-C$_0$–C$_{20}$-alkyl, nitroso, formyl-C$_0$–C$_{20}$-alkyl, carboxyl-C$_0$–C$_{20}$-alkyl and esters and salts thereof, carbamoyl-C$_0$–C$_{20}$-alkyl, sulfo-C$_0$–C$_{20}$-alkyl and esters and salts thereof, sulfamoyl-C$_0$–C$_{20}$-alkyl, amino-C$_0$–C$_{20}$-alkyl, aryl-C$_0$–C$_{20}$-alkyl, C$_0$–C$_{20}$-alkyl, alkoxy-C$_0$–C$_8$-alkyl, carbonyl-C$_0$–C$_6$-alkoxy, and CO-C$_{20}$-alkylamide. Preferably, none of R6–R8 is linked together.

Preferably, Q$_1$, Q$_2$ and Q$_3$ are defined such that a=b=0, c=1,2,3 or 4 and n=1. Preferably, the groups Q$_1$, Q$_2$ and Q$_3$ independently represent a group selected from —CH$_2$— and —CH$_2$CH$_2$—.

Group Q is preferably a group selected from —CH$_2$CH$_2$— and —CH$_2$CH$_2$CH$_2$—.

In a first preferred embodiment, the ligand L is of the general formula (II):

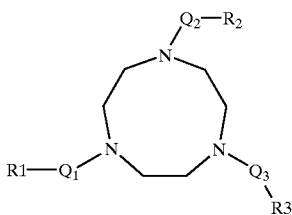

(II)

wherein R1, R2, R3 are as defined previously for $R_1$, $R_2$, $R_3$, and $Q_1$, $Q_2$, $Q_3$ are as defined previously.

A preferred class of ligand according to the first preferred embodiment, as represented by formula (II) above, has ligands of the general formula (II) wherein:

two of R1, R2, R3 each independently represent a coordinating group selected from carboxylate, amido, —NH—C(NH)NH$_2$, hydroxyphenyl, an optionally substituted heterocyclic ring or an optionally substituted heteroaromatic ring selected from pyridine, pyrimidine, pyrazine, pyrazole, imidazole, benzimidazole, quinoline, quinoxaline, triazole, isoquinoline, carbazole, indole, isoindole, oxazole and thiazole; and one of R1, R2, R3 represents a group selected from hydrogen, $C_{1-20}$ optionally substituted alkyl, $C_{1-20}$ optionally substituted arylalkyl, aryl, and $C_{1-20}$ optionally substituted NR$_3^+$ (wherein R=$C_{1-8}$-alkyl).

In this class, we prefer that:

two of R1, R2, R3 each independently represent a coordinating group selected from optionally substituted pyridin-2-yl, optionally substituted imidazol-2-yl, optionally substituted imidazol-4-yl, optionally substituted pyrazol-1-yl, and optionally substituted quinolin-2-yl; and one of R1, R2, R3 represents a group selected from hydrogen, $C_{1-10}$ optionally substituted alkyl, $C_{1-5}$-furanyl, $C_{1-5}$ optionally substituted benzylalkyl, benzyl, $C_{1-5}$ optionally substituted alkoxy, and $C_{1-20}$ optionally substituted N$^+$Me$_3$.

A particularly preferred ligand is 1,4-bis(5-methylpyridin-2-ylmethyl)-7-ethyl-1,4,7-triazacyclononane.

The counter ions Y in formula (A1) balance the charge z on the complex formed by the ligand L, metal M and coordinating species X. Thus, if the charge z is positive, Y may be an anion such as RCOO$^-$, BPh$_4^-$, ClO$_4^-$, BF$_4^-$, PF$_6^-$, RSO$_3^-$, RSO$_4^-$, SO$_4^{2-}$, NO$_3^-$, F$^-$, Cl$^-$, Br$^-$, or I$^-$, with R being hydrogen, optionally substituted alkyl or optionally substituted aryl.

If z is negative, Y may be a common cation such as an alkali metal, alkaline earth metal or (alkyl)ammonium cation.

Suitable counter ions Y include those which give rise to the formation of storage-stable solids. Preferred counter ions for the preferred metal complexes are selected from R$^7$COO$^-$, ClO$_4^-$, BF$_4^-$, PF$_6^-$, RSO$_3^-$ (in particular CF$_3$SO$_3^-$), RSO$_4^-$, SO$_4^{2-}$, NO$_3^-$, F$^-$, Cl$^-$, Br$^-$, and I$^-$, wherein R represents hydrogen or optionally substituted phenyl, naphthyl or $C_1$-$C_4$ alkyl.

It will be appreciated that the complex (A1) can be formed by any appropriate means, including in situ formation whereby precursors of the complex are transformed into the active complex of general formula (A1) under conditions of storage or use. Preferably, the complex is formed as a well-defined complex or in a solvent mixture comprising a salt of the metal M and the ligand L or ligand L-generating species. Alternatively, the catalyst may be formed in situ from suitable precursors for the complex, for example in a solution or dispersion containing the precursor materials. In one such example, the active catalyst may be formed in situ in a mixture comprising a salt of the metal M and the ligand L, or a ligand L-generating species, in a suitable solvent. Thus, for example, if M is iron, an iron salt such as FeSO$_4$ can be mixed in solution with the ligand L, or a ligand L-generating species, to form the active complex. Thus, for example, the composition may formed from a mixture of the ligand L and a metal salt MXn in which preferably n=1–5, more preferably 1–3. In another such example, the ligand L, or a ligand L-generating species, can be mixed with metal M ions present in the substrate or wash liquor to form the active catalyst in situ. Suitable ligand L-generating species include metal-free compounds or metal coordination complexes that comprise the ligand L and can be substituted by metal M ions to form the active complex according to the formula (A1).

The catalysts according to the present invention may be used for laundry cleaning, hard surface cleaning (including cleaning of lavatories, kitchen work surfaces, floors, mechanical ware washing etc.). As is generally known in the art, bleaching compositions are also employed in wastewater treatment, pulp bleaching during the manufacture of paper, leather manufacture, dye transfer inhibition, food processing, starch bleaching, sterilisation, whitening in oral hygiene preparations and/or contact lens disinfection.

In the context of the present invention, bleaching should be understood as relating generally to the decolourisation of stains or of other materials attached to or associated with a substrate. However, it is envisaged that the present invention can be applied where a requirement is the removal and/or neutralisation by an oxidative bleaching reaction of malodours or other undesirable components attached to or otherwise associated with a substrate. Furthermore, in the context of the present invention bleaching is to be understood as being restricted to any bleaching mechanism or process that does not require the presence of light or activation by light.

In typical washing compositions the level of the catalyst is such that the in-use level is from 0.05 $\mu$M to 50 mM, with preferred in-use levels for domestic laundry operations falling in the range 0.5 $\mu$M to 100 $\mu$M, more preferably from 1 $\mu$M to 10 $\mu$M. Higher levels may be desired and applied in industrial bleaching processes, such as textile and paper pulp bleaching.

Preferably, the aqueous medium has a pH in the range from pH 6 to 13, more preferably from pH 6 to 11, still more preferably from pH 8 to 11, and most preferably from pH 8 to 10, in particular from pH 9 to 10.

The bleaching catalyst of the present invention has particular application in detergent formulations, especially for laundry cleaning. The detergent bleach composition may for example contain a surface-active material in an amount of from 10 to 50% by weight. The surface-active material may be naturally derived, such as soap, or a synthetic material selected from anionic, nonionic, amphoteric, zwitterionic, cationic actives and mixtures thereof. Many suitable actives are commercially available and are fully described in the literature, for example in "Surface Active Agents and Detergents", Volumes I and II, by Schwartz, Perry and Berch.

Typical synthetic anionic surface-actives are usually water-soluble alkali metal salts of organic sulfates and sulfonates having alkyl groups containing from about 8 to about 22 carbon atoms, the term "alkyl" being used to include the alkyl portion of higher aryl groups. Examples of suitable synthetic anionic detergent compounds are sodium and ammonium alkyl sulfates, especially those obtained by sulfating higher ($C_8$–$C_{18}$) alcohols produced, for example, from tallow or coconut oil; sodium and ammonium alkyl ($C_9$–$C_{20}$) benzene sulfonates, particularly sodium linear secondary alkyl ($C_{10}$–$C_{15}$) benzene sulfonates; sodium alkyl glyceryl ether sulfates, especially those ethers of the higher alcohols derived from tallow or coconut oil fatty acid monoglyceride sulfates and sulfonates; sodium and ammonium salts of sulfuric acid esters of higher ($C_9$–$C_{18}$) fatty alcohol alkylene oxide, particularly ethylene oxide, reaction products; the reaction products of fatty acids such as coconut fatty acids esterified with isethionic acid and neutralised with sodium hydroxide; sodium and ammonium salts of fatty acid amides of methyl taurine; alkane monosulfonates such as those derived by reacting alpha-olefins ($C_8$–$C_{20}$) with sodium bisulfite and those derived by reacting paraffins with $SO_2$ and $Cl_2$ and then hydrolysing with a base to produce a random sulfonate; sodium and ammonium ($C_7$–$C_{12}$) dialkyl sulfosuccinates; and olefin sulfonates, which term is used to describe material made by reacting olefins, particularly ($C_{10}$–$C_{20}$) alpha-olefins, with $SO_3$ and then neutralising and hydrolysing the reaction product. The preferred anionic detergent compounds are sodium ($C_{10}$–$C_{15}$) alkylbenzene sulfonates, and sodium ($C_{16}$–$C_{18}$) alkyl ether sulfates.

Examples of suitable nonionic surface-active compounds which may be used, preferably together with the anionic surface-active compounds, include, in particular, the reaction products of alkylene oxides, usually ethylene oxide, with alkyl ($C_6$–$C_{22}$) phenols, generally 5–25 EO, i.e. 5–25 units of ethylene oxides per molecule; and the condensation products of aliphatic ($C_8$–$C_{18}$) primary or secondary linear or branched alcohols with ethylene oxide, generally 2–30 EO. Other so-called nonionic surface-actives include alkyl polyglycosides, sugar esters, long-chain tertiary amine oxides, long-chain tertiary phosphine oxides and dialkyl sulfoxides.

Amphoteric or zwitterionic surface-active compounds can also be used but this is not normally desired owing to their relatively high cost. If any amphoteric or zwitterionic detergent compounds are used, it is generally in small amounts in compositions based on the much more commonly used synthetic anionic and nonionic actives.

The detergent bleach composition will preferably comprise from 1 to 15% wt of anionic surfactant and from 10 to 40% by weight of nonionic surfactant. In a further preferred embodiment, the detergent active system is free from $C_{16}$–$C_{12}$ fatty acid soaps.

The bleach composition may also contains a detergency builder, for example in an amount of from about 5 to 80% by weight, preferably from about 10 to 60% by weight. Builder materials may be selected from 1) calcium sequestrant materials, 2) precipitating materials, 3) calcium ion-exchange materials and 4) mixtures thereof.

Examples of calcium sequestrant builder materials include alkali metal polyphosphates, such as sodium tripolyphosphate; nitrilotriacetic acid and its water-soluble salts; the alkali metal salts of carboxymethyloxy succinic acid, ethylene diamine tetraacetic acid, oxydisuccinic acid, mellitic acid, benzene polycarboxylic acids, citric acid; and polyacetal carboxylates as disclosed in U.S. Pat. No. 4,144,226 and U.S. Pat. No. 4,146,495.

Examples of precipitating builder materials include sodium orthophosphate and sodium carbonate.

Examples of calcium ion-exchange builder materials include the various types of water-insoluble crystalline or amorphous aluminosilicates, of which zeolites are the best known representatives, e.g. zeolite A, zeolite B (also known as zeolite P), zeolite C, zeolite X, zeolite Y and also the zeolite P-type as described in EP-A-0,384,070.

In particular, the compositions may contain any one of the organic and inorganic builder materials, though, for environmental reasons, phosphate builders are preferably omitted or only used in very small amounts. Typical builders usable in the present invention are, for example, sodium carbonate, calcite/carbonate, the sodium salt of nitrilotriacetic acid, sodium citrate, carboxymethyloxy malonate, carboxymethyloxy succinate and water-insoluble crystalline or amorphous aluminosilicate builder materials, each of which can be used as the main builder, either alone or in admixture with minor amounts of other builders or polymers as co-builder.

It is preferred that the composition contains not more than 5% by weight of a carbonate builder, expressed as sodium carbonate, more preferably not more than 2.5% by weight to substantially nil, if the composition pH lies in the lower alkaline region of up to 10.

Apart from the components already mentioned, the bleach composition can contain any of the conventional additives in amounts of which such materials are normally employed in fabric washing detergent compositions. Examples of these additives include buffers such as carbonates, lather boosters, such as alkanolamides, particularly the monoethanol amides derived from palmkernel fatty acids and coconut fatty acids; lather depressants, such as alkyl phosphates and silicones; anti-redeposition agents, such as sodium carboxymethyl cellulose and alkyl or substituted alkyl cellulose ethers; stabilisers, such as phosphonic acid derivatives (i.e. Dequest® types); fabric softening agents; inorganic salts and alkaline buffering agents, such as sodium sulfate and sodium silicate; and, usually in very small amounts, fluorescent agents; perfumes; enzymes, such as proteases, cellulases, lipases, amylases and oxidases; germicides and colourants.

Transition metal sequestrants such as EDTA, and phosphonic acid derivatives such as EDTMP (ethylene diamine tetra(methylene phosphonate)) may also be included, in addition to the ligand specified, for example to improve the stability sensitive ingredients such as enzymes, fluorescent agents and perfumes, but provided the composition remains bleaching effective. However, the composition is preferably substantially, and more preferably completely, devoid of transition metal sequestrants (other than the ligand).

Whilst the present invention is based on the catalytic bleaching of a substrate by atmospheric oxygen or air, it will be appreciated that small amounts of hydrogen peroxide or peroxy-based or -generating systems may be included in the composition, if desired. Therefore, by "substantially devoid of peroxygen bleach or peroxy-based or -generating bleach systems" is meant that the composition contains from 0 to 50%, preferably from 0 to 10%, more preferably from 0 to 5%, and optimally from 0 to 2% by molar weight on an oxygen basis, of peroxygen bleach or peroxy-based or -generating bleach systems. Preferably, however, the composition will be wholly devoid of peroxygen bleach or peroxy-based or -generating bleach systems.

Thus, at least 10%, preferably at least 50% and optimally at least 90% of any bleaching of the substrate is effected by oxygen sourced from the air.

Throughout the description and claims generic groups have been used, for example alkyl, alkoxy, aryl. Unless otherwise specified the following are preferred group restrictions that may be applied to generic groups found within compounds disclosed herein:

alkyl: linear and branched C1–C8-alkyl, alkenyl: C2–C6-alkenyl, cycloalkyl: C3–C8-cycloalkyl, alkoxy: C1–C6-alkoxy, alkylene: selected from the group consisting of: methylene; 1,1-ethylene; 1,2-ethylene; 1,1-propylidene; 1,2-propylene; 1,3-propylene; 2,2-propylidene; butan-2-ol-1,4-diyl; propan-2-ol-1,3-diyl; 1,4-butylene; cyclohexane-1,1-diyl; cyclohexan-1,2-diyl; cyclohexan-1,3-diyl; cyclohexan-1,4-diyl; cyclopentane-1,1-diyl; cyclopentan-1,2-diyl; and cyclopentan-1,3-diyl, aryl: selected from homoaromatic compounds having a molecular weight under 300, arylene: selected from the group consisting of: 1,2-phenylene; 1,3-phenylene; 1,4-phenylene; 1,2-naphtalenylene; 1,3-naphtalenylene; 1,4-naphtalenylene; 2,3-naphtalenylene; 1-hydroxy-2,3-phenylene; 1-hydroxy-2,4-phenylene; 1-hydroxy-2,5-phenylene; and 1-hydroxy-2,6-phenylene, heteroaryl: selected from the group consisting of: pyridinyl; pyrimidinyl; pyrazinyl; triazolyl; pyridazinyl; 1,3,5-triazinyl; quinolinyl; isoquinolinyl; quinoxalinyl; imidazolyl; pyrazolyl; benzimidazolyl; thiazolyl; oxazolidinyl; pyrrolyl; carbazolyl; indolyl; and isoindolyl, wherein the heteroaryl may be connected to the compound via any atom in the ring of the selected heteroaryl, heteroarylene: selected from the group consisting of: pyridindiyl; quinolindiyl; pyrazodiyl; pyrazoldiyl; triazolediyl; pyrazindiyl; and imidazolediyl, wherein the heteroarylene acts as a bridge in the compound via any atom in the ring of the selected heteroarylene, more specifically preferred are: pyridin-2,3-diyl; pyridin-2,4-diyl; pyridin-2,5-diyl; pyridin-2,6-diyl; pyridin-3,4-diyl; pyridin-3,5-diyl; quinolin-2,3-diyl; quinolin-2,4-diyl; quinolin-2,8-diyl; isoquinolin-1,3-diyl; isoquinolin-1,4-diyl; pyrazol-1,3-diyl; pyrazol-3,5-diyl; triazole-3,5-diyl; triazole-1,3-diyl; pyrazin-2,5-diyl; and imidazole-2,4-diyl, heterocycloalkyl: selected from the group consisting of: pyrrolinyl; pyrrolidinyl; morpholinyl; piperidinyl; piperazinyl; hexamethylene imine; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thia-cyclononanyl; 1,4-diaza-7-oxa-cyclononanyl; 1,4,7,10-tetraazacyclododecanyl; 1,4-dioxanyl; 1,4,7-trithia-cyclononanyl; tetrahydropyranyl; and oxazolidinyl, wherein the heterocycloalkyl may be connected to the compound via any atom in the ring of the selected heterocycloalkyl, heterocycloalkylene: selected from the group consisting of: piperidin-1,2-ylene; piperidin-2,6-ylene; piperidin-4,4-ylidene; 1,4-piperazin-1,4-ylene; 1,4-piperazin-2,3-ylene; 1,4-piperazin-2,5-ylene; 1,4-piperazin-2,6-ylene; 1,4-piperazin-1,2-ylene; 1,4-piperazin-1,3-ylene; 1,4-piperazin-1,4-ylene; tetrahydrothiophen-2,5-ylene; tetrahydrothiophen-3,4-ylene; tetrahydrothiophen-2,3-ylene; tetrahydrofuran-2,5-ylene; tetrahydrofuran-3,4-ylene; tetrahydrofuran-2,3-ylene; pyrrolidin-2,5-ylene; pyrrolidin-3,4-ylene; pyrrolidin-2,3-ylene; pyrrolidin-1,2-ylene; pyrrolidin-1,3-ylene; pyrrolidin-2,2-ylidene; 1,4,7-triazacyclonon-1,4-ylene; 1,4,7-triazacyclonon-2,3-ylene; 1,4,7-triazacyclonon-2,9-ylene; 1,4,7-triazacyclonon-3,8-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,5-ylene; 1,4,8,11-tetraazacyclotetradec-1,2-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-1,2-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4,7,10,13-pentaazacyclopentadec-2,3-ylene; 1,4,7,10,13-pentaazacyclopentadec-1,2-ylene; 1,4,7,10,13-pentaazacyclopentadec-2,2-ylidene; 1,4-diaza-7-thia-cyclonon-1,4-ylene; 1,4-diaza-7-thia-cyclonon-1,2-ylene; 1,4-diaza-7-thia-cyclonon-2,3-ylene; 1,4-diaza-7-thia-cyclonon-6,8-ylene; 1,4-diaza-7-thia-cyclonon-2,2-ylidene; 1,4-diaza-7-oxa-cyclonon-1,4-ylene; 1,4-diaza-7-oxa-cyclonon-1,2-ylene; 1,4-diaza-7-oxa-cyclonon-2,3-ylene; 1,4-diaza-7-oxa-cyclonon-6,8-ylene; 1,4-diaza-7-oxa-cyclonon-2,2-ylidene; 1,4-dioxan-2,3-ylene; 1,4-dioxan-2,6-ylene; 1,4-dioxan-2,2-ylidene; tetrahydropyran-2,3-ylene; tetrahydropyran-2,6-ylene; tetrahydropyran-2,5-ylene; tetrahydropyran-2,2-ylidene; 1,4,7-trithia-cyclonon-2,3-ylene; 1,4,7-trithia-cyclonon-2,9-ylene; and 1,4,7-trithia-cyclonon-2,2-ylidene, amine: the group —N(R)$_2$ wherein each R is independently selected from: hydrogen; C1–C6-alkyl; C1–C6-alkyl-C6H5; and phenyl, wherein when both R are C1–C6-alkyl both R together may form an —NC3 to an —NC5 heterocyclic ring with any remaining alkyl chain forming an alkyl substituent to the heterocyclic ring, halogen: selected from the group consisting of: F; Cl; Br and I, sulfonate: the group —S(O)$_2$OR, wherein R is selected from: hydrogen; C1–C6-alkyl; phenyl; C1–C6-alkyl-C6H5; Li; Na; K; Cs; Mg; and Ca, sulfate: the group —OS(O)$_2$OR, wherein R is selected from: hydrogen; C1–C6-alkyl; phenyl; C1–C6-alkyl-C6H5; Li; Na; K; Cs; Mg; and Ca, sulfone: the group —S(O)$_2$R, wherein R is selected from: hydrogen; C1–C6-alkyl; phenyl; C1–C6-alkyl-C6H5 and amine (to give sulfonamide) selected from the group: —NR'2, wherein each R' is independently selected from: hydrogen; C1–C6-alkyl; C1–C6-alkyl-C6H5; and phenyl, wherein when both R' are C1–C6-alkyl both R' together may form an —NC3 to an —NC5 heterocyclic ring with any remaining alkyl chain forming an alkyl substituent to the heterocyclic ring, carboxylate derivative: the group —C(O)OR, wherein R is selected from: hydrogen; C1–C6-alkyl; phenyl; C1–C6-alkyl-C6H5; Li; Na; K; Cs; Mg; and Ca, carbonyl derivative: the group —C(O)R, wherein R is selected from: hydrogen; C1–C6-alkyl; phenyl; C1–C6-alkyl-C6H5 and amine (to give amide) selected from the group: —NR'2, wherein each R' is independently selected from: hydrogen; C1–C6-alkyl; C1–C6- alkyl-C6H5; and phenyl, wherein when both R' are C1–C6-alkyl both R' together may form an —NC3 to an —NC5 heterocyclic ring with any remaining alkyl chain forming an alkyl substituent to the heterocyclic ring, phosphonate: the group —P(O)(OR)$_2$, wherein each R is independently selected from: hydrogen; C1–C6-alkyl; phenyl; C1–C6-alkyl-C6H5; Li; Na; K; Cs; Mg; and Ca, phosphate: the group —OP(O)(OR)2, wherein each R is independently selected from: hydrogen; C1–C6-alkyl; phenyl; C1–C6-alkyl-C6H5; Li; Na; K; Cs; Mg; and Ca, phosphine: the group —P(R)$_2$, wherein each R is independently selected from: hydrogen; C1–C6-alkyl; phenyl; and C1–C6-alkyl-C6H5, phosphine oxide: the group —P(O)R$_2$, wherein R is independently selected from: hydrogen; C1–C6-alkyl; phenyl; and C1–C6-alkyl-C6H5; and amine (to give phosphonamidate) selected from the group: —NR'2, wherein each R' is independently selected from: hydrogen; C1–C6-alkyl; C1–C6-alkyl-C6H5; and phenyl, wherein when both R' are C1–C6-alkyl both R' together may form an —NC3 to an —NC5 heterocyclic ring with any remaining alkyl chain forming an alkyl substituent to the heterocyclic ring.

Unless otherwise specified the following are more preferred group restrictions that may be applied to groups found within compounds disclosed herein:

alkyl: linear and branched C1–C6-alkyl, alkenyl: C3–C6-alkenyl, cycloalkyl: C6–C8-cycloalkyl, alkoxy: C1–C4-alkoxy, alkylene: selected from the group consisting of: methylene; 1,2-ethylene; 1,3-propylene; butan-2-ol-1,4-diyl; 1,4-butylene; cyclohexane-1,1-diyl; cyclohexan-1,2-diyl; cyclohexan-1,4-diyl; cyclopentane-1,1-diyl; and cyclopentan-1,2-diyl, aryl: selected from group consisting of: phenyl; biphenyl; naphthalenyl; anthracenyl; and phenanthrenyl, arylene: selected from the group consisting of: 1,2-phenylene; 1,3-phenylene; 1,4-phenylene; 1,2-naphtalenylene; 1,4-naphtalenylene; 2,3-naphtalenylene and 1-hydroxy-2,6-phenylene, heteroaryl: selected from the group consisting of: pyridinyl; pyrimidinyl; quinolinyl; pyrazolyl; triazolyl; isoquinolinyl; imidazolyl; and oxazolidinyl, wherein the heteroaryl may be connected to the compound via any atom in the ring of the selected heteroaryl, heteroarylene: selected from the group consisting of: pyridin-2,3-diyl; pyridin-2,4-diyl; pyridin-2,6-diyl; pyridin-3,5-diyl; quinolin-2,3-diyl; quinolin-2,4-diyl; isoquinolin-1,3-diyl; isoquinolin-1,4-diyl; pyrazol-3,5-diyl; and imidazole-2,4-diyl, heterocycloalkyl: selected from the group consisting of: pyrrolidinyl; morpholinyl; piperidinyl; piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and piperazinyl, wherein the heterocycloalkyl may be connected to the compound via any atom in the ring of the selected heterocycloalkyl, heterocycloalkylene: selected from the group consisting of: piperidin-2,6-ylene; piperidin-4,4-ylidene; 1,4-piperazin-1,4-ylene; 1,4-piperazin-2,3-ylene; 1,4-piperazin-2,6-ylene; tetrahydrothiophen-2,5-ylene; tetrahydrothiophen-3,4-ylene; tetrahydrofuran-2,5-ylene; tetrahydrofuran-3,4-ylene; pyrrolidin-2,5-ylene; pyrrolidin-2,2-ylidene; 1,4,7-triazacyclonon-1,4-ylene; 1,4,7-triazacyclonon-2,3-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,2-ylidene; 1,4,7,10-tetraazacyclododec-1,4-ylene; 1,4,7,10-tetraazacyclododec-1,7-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4-diaza-7-thia-cyclonon-1,4-ylene; 1,4-diaza-7-thia-cyclonon-2,3-ylene; 1,4-diaza-7-thia-cyclonon-2,2-ylidene; 1,4-diaza-7-oxa-cyclonon-1,4-ylene; 1,4-diaza-7-oxa-cyclonon-2,3-ylene; 1,4-diaza-7-oxa-cyclonon-2,2-ylidene; 1,4-dioxan-2,6-ylene; 1,4-dioxan-2,2-ylidene; tetrahydropyran-2,6-ylene; tetrahydropyran-2,5-ylene; and tetrahydropyran-2,2-ylidene, amine: the group —N(R)$_2$, wherein each R is independently selected from: hydrogen; C1–C6-alkyl; and benzyl, halogen: selected from the group consisting of: F and Cl, sulfonate: the group —S(O)$_2$OR, wherein R is selected from: hydrogen; C1–C6-alkyl; Na; K; Mg; and Ca, sulfate: the group —OS(O)$_2$OR, wherein R is selected from: hydrogen; C1–C6-alkyl; Na; K; Mg; and Ca, sulfone: the group —S(O)$_2$R, wherein R is selected from: hydrogen; C1–C6-alkyl; benzyl and amine selected from the group: —NR'2, wherein each R' is independently selected from: hydrogen; C1–C6-alkyl; and benzyl, carboxylate derivative: the group —C(O)OR, wherein R is selected from hydrogen; Na; K; Mg; Ca; C1–C6-alkyl; and benzyl, carbonyl derivative: the group: —C(O)R, wherein R is selected from: hydrogen; C1–C6-alkyl; benzyl and amine selected from the group: —NR'2, wherein each R' is independently selected from: hydrogen; C1–C6-alkyl; and benzyl, phosphonate: the group —P(O)(OR)$_2$, wherein each R is independently selected from: hydrogen; C1–C6-alkyl; benzyl; Na; K; Mg; and Ca, phosphate: the group —OP(O)(OR)$_2$, wherein each R is independently selected from: hydrogen; C1–C6-alkyl; benzyl; Na; K; Mg; and Ca, phosphine: the group —P(R)$_2$, wherein each R is independently selected from: hydrogen; C1–C6-alkyl; and benzyl, phosphine oxide: the group —P(O)R$_2$, wherein R is independently selected from: hydrogen; C1–C6-alkyl; benzyl and amine selected from the group: —NR'2, wherein each R' is independently selected from: hydrogen; C1–C6-alkyl; and benzyl.

The invention will now be further illustrated by way of the following non-limiting examples:

EXAMPLES

The following compound was prepared:

Compound 1: [FeL$^4$Cl] (ClO$_4$)$_2$

L$^1$=1,4-bis(5-methyl-pyridin-2-ylmethyl)-7-ethyl-1,4,7-triazacyclononane

Synthesis of ligand L¹: 1,4-bis(5-Methyl-pyridyl-2-methyl)-7-ethyl-1,4,7-triazacyclononane 1,4,7-Triazacyclononane Ligand 1,4,7-triazacyclononane was produced according the modified method used by the team of Prof. Wieghardt. In this method the detosylation of the 1,4,7-tris-p-toluenesulfon-1,4,7-triazacylononanamide is performed in 5 minutes in hot sulphuric acid of 180° C. Once the solution has cooled down it is transferred into ether under vigorous stirring. The solution that surfaces is decanted and the residue is dissolved in some boiling water. At boiling temperature drops of concentrated hydrochloric acid are added. The brown crystals that precipitate are drained off and washed with cold hydrochloric acid and then with ethanol and ether. The 1,4,7-triazacyclononane. trihydrochloride thus produced is then processed further as described by Wieghardt et al (K. Wieghardt et al, Chem Ber., 112, 2200 (1979)).

1,4,7-Triazatricyclo[5.2.1.0$^{4,10}$]decane (Orthoamide) 0.5 mol 1,4,7-triazacyclononane, 64.3 g, 0.54 mol orthoformicacidtriethylester, 74.8 g, and 20 mmol p-toluolsulphonacid, 4 g, are heated to 150° C. The ethanol that is created and some of the esters are distilled off. After the reaction has been completed the orthoamide can be distilled off at a pressure of <80 mbar in the form of a bright yellow volatile oil (b.p. 350 K at 133 Pa), in agreement with literature (T. J. Atkins, *J. Am. Chem. Soc.*, 102, 6365 (1980)).

1-Ethyl-1,4,7-triazacyclononan (Et-tacn)

Into a mixture of 0.1 mol orthoamide, 13.92 g, dissolved in dry THF, slowly 0.1 mol ethylbromide, 10.9 g, is dripped. The suspension is stirred for 2 days at room temperature in a closed flask. The microcrystalline powder is drained off and washed with some dry THF. The resulting bromide salt is very hygroscopic. The salt is dissolved in 80 ml water and boiled for 4 hours under back-flow. Then 16 g sodium hydroxide dissolved in 20 ml water is added. This creates a 4 molar reaction mixture. Immediately, a bright yellow oil is separated. To complete the reaction, boiling is continued for another 20 hours. After cooling down 300 ml toluol is added and the water is distilled off by means of a water separator. The reaction mixture is filtered and the toluol is drained off by a rotary evaporator. The remaining product is a bright yellow oil. Yield: 13.8 g (89%). ¹H-NMR (CDCl$_3$ 270 MHz; 300K): 2.59–2.39 (m; 14H); 1.83 (s, 2H); 0.90 ppm (t; 3H); ¹³C-NMR: 52.1; 50.7; 46.5; 46.4; 12.4 ppm.

2-Hydroxymethyl-5-Methyl pyridine

2-Acetoxymethyl-5-methyl pyridine (30 g, 182 mmol) was dissolved in hydrochloric acid (100 mL, 4 N). The mixture was heated under reflux, until TLC (silica gel; triethylamine:ethyl acetate:petroleum ether 40–60=1:9:19) showed complete absence of the acetate (normally 1 hour). The mixture was cooled, brought to pH>11, extracted with dichloromethane (3×50 mL) and the solvent removed in vacuo. Pure 2-hydroxymethyl-5-methyl pyridine (18.80 g, 152 mmol, 84%) was obtained by Kugelrohr distillation (p=20 mm Hg, T=130° C.) as a slightly yellow oil.

¹H NMR: δ 8.39 (s, 1H), 7.50 (dd, J=7.8, J=1.8, 1H), 7.15 (d, J=8.1, 1H), 4.73 (s, 2H), 3.83 (br s, 1H), 2.34 (s, 3H); ¹³C NMR: δ 156.67, 148.66, 137.32, 131.62, 120.24, 64.12, 17.98.

1,4-bis(5-Methyl-pyridyl-2-methyl)-7-ethyl-1,4,7-triazacyclononane 2-hydroxymethyl-5-methyl pyridine (2.70 g, 21.9 mmol) was dissolved in dichloromethane (25 mL). Thionyl chloride (25 mL) was added dropwise under cooling (ice bath). The resulting mixture was stirred for 1 hour and the solvents removed in vacuo (rotavap, until p=20 mm Hg, T±35° C.). The remaining oil was used directly in the synthesis of the ligands, since it was known from the literature that the free picolyl chlorides are somewhat unstable and are highly lachrymatory. To the resultant mixture was added dichloromethane (25 mL) and 1.55 g Et-tacn (10 mmol) was added. Under cooling with ice 8.0 g NaOH is added in portions over a period of 5 days in such a way that the pH-value remains below 9 and the temperature does not exceed 0° C. The solution gradually becomes red to brown. The solution is put in the refrigerator for one day. Any organic phase that has formed is separated. The watery phase is extracted by repeated shaking with chloroform. The combined organic phases are dried over CaO. The chloroform is rotated off and a thick, mostly red-brown oil remains. This oil is still contaminated by traces of picolylchloride and by-products of the alkaline hydrolysis of the picolylchlorides (approx. 5%).

What is claimed is:

1. A ligand, wherein the ligand L is of a general formula (I):

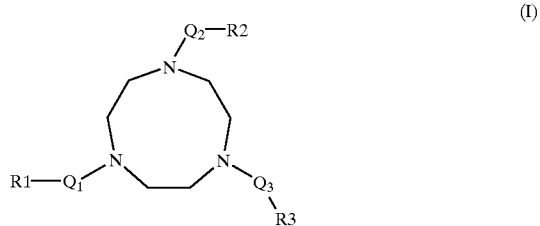

wherein two of R1, R2, R3 each independently represent a coordinating moiety selected from the group consisting of carboxylate, amido, —NH—C(NH)NH$_2$, hydroxyphenot, and an optionally substituted heterocyclic ring or an optionally substituted heteroaromatic ring selected from pyridine, pyrimidine, pyrazine, pyrazole, imidazole, benzimidazole, quinotine, quinoxaline, triazole, isoquinotine, carbazole, indole, isoindole, oxazole and thiazole;

one of R1, R2, R3 represents a moiety selected from the group consisting of hydrogen, C$_{1-20}$ optionally substituted atkyl, C$_{1-20}$ optionally substituted arylatkyl, aryl, and C$_{1-20}$ optionally substituted N(R)$_3^+$ (wherein R=C$_{1-8}$-alkyl);

Q$_1$, Q$_2$ and Q$_3$ independently represent a group having the formula:

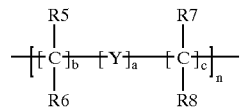

wherein
a=b=0, c=1,2,3 or 4 and n=1;
R5, R6, R7, R8 independently represent a moiety selected from the group consisting of hydrogen, hydroxyl, halogen, —R and —OR, wherein R represents a radical selected from the group consisting of alkyl, alkenyl, cycloalkyt, and aryl;

provided that two of R1, R2 and R3 are coordinating groups and one of R1, R2 and R3 is a non-coordinating group, and with proviso that the foLlowing ligands are excluded:

1,4-bis(N-methyl-imidazol-2ytmethyl)-1,4,7-triazacyclononane;

1,4-bis(N-methyl-imidazol-2ytmethyl)-7-acetate-1,4,7-triazacyctononane;

1,4-bis(pyridin-2-ytmethyl)-7-ethyl-1,4,7-triazacyclononane;

1,4-bis(quinotin-2-ytmethyl)-7-ethyl-1,4,7-triazacyclononane;

1,4-bis(pyrazot-1-ytmethyl)-7-ethyt-1,4,7-triazacyclononane;

1,4-bis(3,5-dimethytpyrazol-1-ytmethyt)-7-ethyl-1,4,7-triazacyclononane;

1,4-bis(N-methytimidazol-2-ytmethyt)-7-ethyt-1,4,7-triazacycLononane;

1,4-bis(N-isopropytacetamido)-7-ethyl-1,4,7-triazacyclononane; and 1,4-bis(N-methytacetamido)-7-ethyl-1,4,7-triazacyclononane.

2. A ligand according to claim 1, wherein two of R1, R2, R3 each independently represent a coordinating group selected from optionally substituted pyridin-2-yl, optionally substituted imidazol-2-yl, optionally substituted imidazol-4-yl, optionally substituted pyrazol-1-yl, and optionally substituted quinolin-2-yl.

3. A ligand according to claim 1, wherein $Q_1$, $Q_2$ and $Q_3$ independently represent a group selected from —$CH_2$— and —$CH_2CH_2$—.

4. A bleaching composition comprising a complex of a ligand and a transition metal, wherein the complex is of the general formula (A1):

$$[M_aL_kX_n]Y_m \quad (A1)$$

in which:

M represents a metal selected from Mn(II)-(III)-(IV)-(V), Cu(I)-(II)-(II), Fe(II)-(III)-(IV)-(V), Co(I)-(II)-(III), Ti(II)-(III)-(IV), V(II)-(III)-(IV)-(V), Mo(II)-(III)-(IV)-(V)-(VI) and W(IV)-(V)-(VI);

X represents a coordinating species selected from any mono, bi or tri charged anions and any neutral molecules able to coordinate the metal in a mono, bi or tridentate manner;

Y represents any non-coordinated counter ion;

a represents an integer from 1 to 10;

k represents an integer from 1 to 10;

n represents an integer from 1 to 10;

m represents zero or an integer from 1 to 20; and

L represents a tigand as defined by claim 8, or its protonated or deprotonated analogue.

5. A complex according to claim 4, wherein:

M represents Fe(II)-(III)-(IV)-(V);

X represents a coordinating species selected from $O^{2-}$, $RBO_2^{2-}$, $RCOO^-$, $OH^-$, $NO_3^-$, $S^{2-}$, $RS^-$, $PO_3^{4-}$, $H_2O$, $CO_3^{2-}$, $HCO_3^-$, $ROH$, $N(R)_3$, $Cl^-$, $Br^-$, $OCN^-$, $SCN^-$, $RCN$, $N_3^-$, $F^-$, $I^-$, $RO^-$, $ClO_4^-$, and $CF_3SO_3^-$;

Y represents any non-coordinated counter ion selected from $ClO_4^-$, $BR_4^-$, $[FeCl_4]^-$, $PF_6^-$, $RCOO^-$, $NO_3^-$, $RO^-$, $N^+(R)_4$, $Cl^-$, $Br^-$, $F^-$, $I^-$, $CF_3SO_3^-$, $S_2O_6^{2-}$, $OCN^-$, $SCN^-$, $H_2O$ and $BF_4^-$;

a represents an integer from 1 to 4;

k represents an integer from 1 to 10;

n represents an integer from 1 to 4;

m represents zero or an integer from 1 to 8; and each R independently represents a group selected from hydrogen, optionally substituted alkyl and optionally substituted aryl.

6. The ligand according to claim 1 which is 1,4-bis(5-methyl-pyridin-2-ylmethyl)-7-ethyL-1,4,7-triazacyclononane.

* * * * *

UNITED STATES PATENT AND TRADEMARK OFFICE
CERTIFICATE OF CORRECTION

PATENT NO. : 6,432,900 B1  
DATED : August 13, 2002  
INVENTOR(S) : Appel et al.

Page 1 of 1

It is certified that error appears in the above-identified patent and that said Letters Patent is hereby corrected as shown below:

Column 16,
Line 39, "quinotine" should be -- quinoline --;
Line 39, "isoquinotine" should be -- isoquinoline --;
Line 43, "atkyl" should be -- alkyl --; and
Line 43, "arylatkyl" should be -- arylalkyl --;
Line 61, "cycloalkyt" should be -- cycloalkyl --;
Line 64, "foLlowing" should be -- following --; and
Line 66, "2ytmethyl)" should be -- 2ylmethyl) --.

Column 17,
Line 1, "2ytmethyl" should be -- 2ylmethyl --;
Line 2, "triazacyctononane" should be -- triazacyclononane --;
Line 3, "2-ytmethyl" should be -- 2-ylmethyl --;
Line 5, "quinotin" should be -- quinolin -- and "2-ytmethyl" should be -- 2-ylmethyl --;
Line 7, "pyrazot" should be -- pyrazol --; "1-ytmethyl" should be -- 1-ylmethyl -- and "7-ethyt" should be -- 7-ethyl --;
Line 9, "1-ytmethyt" should be -- 1-ylmethyl --;
Line 11, "(N-methytimidazol-2-ytmethyt)-7-ethyt-1,4,7-triazacycLononane" should be -- N-methylimidazol-2-ylmethyl-7-ethyl-1,4,7-triazacyclononane --;
Line 12, "triazacycLononane" should be -- triazacyclononane --;
Line 13, "isopropytacetamido" should be -- ispropylacetamido --; and
Line 15, "methytacetamido" should be -- methylacetamido --.

Column 18,
Line 11, "tigand" should be -- ligand --; and "claim 8" should be -- claim 1 --.
Line 33, "7-ethyL" should be -- 7-ethyl --.

Signed and Sealed this

Eighteenth Day of February, 2003

JAMES E. ROGAN  
*Director of the United States Patent and Trademark Office*